US011710265B2

United States Patent
van der Meulen et al.

(10) Patent No.: US 11,710,265 B2
(45) Date of Patent: Jul. 25, 2023

(54) METHOD FOR PRODUCING AN IMAGE OF EXPECTED RESULTS OF MEDICAL COSMETIC TREATMENTS ON A HUMAN ANATOMICAL FEATURE FROM AN IMAGE OF THE ANATOMICAL FEATURE PRIOR TO THESE MEDICAL COSMETIC TREATMENTS

(71) Applicant: RealFaceValue B.V., Rotterdam (NL)

(72) Inventors: Jacques van der Meulen, Rotterdam (NL); Ekin Gedik, Delft (NL); Berno Bucker, Amsterdam (NL)

(73) Assignee: RealFaceValue B.V., Rotterdam (NL)

( * ) Notice: Subject to any disclaimer, the term of this patent is extended or adjusted under 35 U.S.C. 154(b) by 88 days.

(21) Appl. No.: 17/342,330

(22) Filed: Jun. 8, 2021

(65) Prior Publication Data
US 2022/0392126 A1    Dec. 8, 2022

(51) Int. Cl.
| | |
|---|---|
| G06T 11/00 | (2006.01) |
| G06T 11/60 | (2006.01) |
| G16H 20/40 | (2018.01) |
| G16H 30/20 | (2018.01) |
| G16H 70/20 | (2018.01) |
| G06T 7/00 | (2017.01) |

(52) U.S. Cl.
CPC ............ *G06T 11/60* (2013.01); *G06T 7/0016* (2013.01); *G06T 11/001* (2013.01); *G16H 20/40* (2018.01); *G16H 30/20* (2018.01); *G16H 70/20* (2018.01); *G06T 2207/20084* (2013.01); *G06T 2207/20224* (2013.01); *G06T 2207/30201* (2013.01)

(58) Field of Classification Search
CPC ........ G06T 11/60; G06T 11/001; G16H 30/20
See application file for complete search history.

(56) References Cited

U.S. PATENT DOCUMENTS

| | | | |
|---|---|---|---|
| 2007/0207437 A1* | 9/2007 | Sachdeva | A61C 8/009 433/24 |
| 2017/0178306 A1* | 6/2017 | Le Clerc | G06V 10/7715 |
| 2019/0251723 A1 | 8/2019 | Franklin et al. | |
| 2020/0035016 A1* | 1/2020 | Muller | G06N 3/10 |

(Continued)

OTHER PUBLICATIONS

"A Survey on Generative Adversarial Networks: Variants, Applications, and Training", Cornell University Library, Jun. 9, 2020; Abdul Jabbar et al.

(Continued)

*Primary Examiner* — Samantha (Yuehan) Wang
(74) *Attorney, Agent, or Firm* — Richard A. Fagin

(57) ABSTRACT

A method for imaging expected results of a medical cosmetic treatment includes converting an input image of an anatomical feature into an input image vector. A direction vector corresponding to the medical cosmetic treatment is determined. An amplitude of the direction vector is determined. The direction vector is multiplied by the determined amplitude to obtain a product vector. The product vector is vector added to the input image vector. An output image corresponding to the expected visual appearance of the human anatomical feature is generated from the vector added product vector and input image vector. A computer program stored in a non-transitory computer readable medium causes a computer to perform the imaging method.

16 Claims, 4 Drawing Sheets

(56) References Cited

U.S. PATENT DOCUMENTS

2021/0118132 A1* 4/2021 Kearney .............. G06N 3/0454
2021/0213304 A1* 7/2021 Domnik ............... A61N 5/1065

OTHER PUBLICATIONS

"BeautyGAN Instance-level Facial Makeup Transfer with Deep Generative Adversarial Network", Multimedia ACM, Oct. 15, 2018, Li Tingling Litt Thu@foxmail.com et al.
International Search Report and Written Opinion dated Sep. 26, 2022, for International Application PCT/IB2022/054934.

* cited by examiner

METHOD FOR PRODUCING AN IMAGE OF EXPECTED RESULTS OF MEDICAL COSMETIC TREATMENTS ON A HUMAN ANATOMICAL FEATURE FROM AN IMAGE OF THE ANATOMICAL FEATURE PRIOR TO THESE MEDICAL COSMETIC TREATMENTS

CROSS REFERENCE TO RELATED APPLICATIONS

Not Applicable.

STATEMENT REGARDING FEDERALLY SPONSORED RESEARCH OR DEVELOPMENT

Not Applicable

NAMES OF THE PARTIES TO A JOINT RESEARCH AGREEMENT

Not Applicable.

BACKGROUND

This disclosure relates to the field of processing images of a human anatomical feature, such as the face, to project expected appearance of the face as a result of contemplated treatment, such as a medical cosmetic treatment, surgical treatment or medical treatment such as injection of fillers and other agents. More specifically, the disclosure relates to methods for creating an expected image based on machine learning processing of actual changes in appearance resulting from facial treatments on actual persons.

Cosmetic treatments, e.g., medical cosmetic treatments, surgical treatments and injections (for example, but not limited to Botox and fillers), are undertaken to modify appearance of human features, such as the face. While physicians, in particular plastic surgeons, have detailed knowledge of how to perform such procedures, and have informed understanding of how such procedures will alter the appearance of human features, it is difficult to convey to the person what may be reasonably expected as a result of such procedures. Further, the physician may have the ability to choose the amount by which features are changed with reference to the intensity of a procedure or the product used, but may still be unable to convey to the person how variations in the amount of feature change will affect the overall appearance when the treatments are completed.

Accordingly, there is a need for a tool to enable visualization of how facial treatments will alter appearance based on the pre-treatment actual appearance of a person

SUMMARY

One aspect of the present disclosure is a method for generating an image of expected appearance of a human anatomical feature resulting from a medical cosmetic treatment from an image of the human anatomical feature prior to the treatment. A method according to this aspect of the disclosure includes the following: sending as input to a computer an image of the human anatomical feature prior to performing the medical cosmetic treatment; in the computer, converting the input image into an input image vector; in the computer, selecting a direction vector corresponding to the medical cosmetic treatment; in the computer, determining an amplitude of the direction vector; in the computer, multiplying the direction vector by the determined amplitude to obtain a product vector; in the computer, vector adding the product vector to the input image vector; and in the computer, generating an output image corresponding to the expected visual appearance from the vector added product vector and the input image vector, In another aspect of this disclosure, a computer program is stored in a non-transitory computer readable medium. The program has logic operable to cause a programmable computer to perform the actions of a method according to this disclosure as recited above, and in various embodiments, as described below.

Some embodiments further comprise optimizing the converting the input image by, in the computer: (a) generating an optimizing image from the input image vector; (b) comparing the optimizing image with the input image to calculate a loss function; (c) changing the input image vector and repeating the generating the optimizing image; and (d) repeating (a), (b) and (c) until either (i) a value of the loss function falls below a predetermined threshold or (ii) (a), (b) and (c) are repeated a selected number of times.

In some embodiments, determining of an upper limit for the amplitude comprises, in the computer, (a) converting pre treatment and post treatment pairs of images of corresponding human anatomical features to image vectors; (b) calculating difference vectors between the converted pre treatment and post treatment image vectors; (c) calculating the amplitudes for each pre-treatment and post-treatment image vector pair using the respective difference vector and previously identified direction vector, (d) determining the upper limit on the amplitude using the distribution of the amplitude values calculated in (c).

In some embodiments, determining of the amplitude comprises, in the computer, (a) converting a pre treatment image of a corresponding human anatomical feature to an input vector; (b) initially estimating an amplitude and generating an intermediate product vector with the previously estimated direction vector, (c) adding the intermediate product vector to the converted input vector, (d) generating an output image from the intermediate product vector; (e) determining a change in landmark positions, color and texture between the input image and the output image; (f) adjusting the amplitude and repeating (b), (c), (d) and (e) until the change in at least one of the landmarks, color and texture reaches a predefined threshold or the amplitude reaches computed predetermined upper limit.

In some embodiments, the determining the direction vector comprises, for the cosmetic treatment: converting at least one image of the anatomical before the medical cosmetic treatment feature to a first input image vector; converting at least one image of the anatomical feature after the medical cosmetic treatment to a second input image vector treating the before treatment image vector and the after treatment image vector as a binary classification wherein the before and after images represent a negative and a positive class, respectively; setting a linear decision boundary; and determining a vector that is orthogonal to the linear decision boundary.

In some embodiments, the determining the direction vector comprises, for the medical cosmetic treatment: converting at least one image of the anatomical feature before the medical cosmetic treatment to a first input image vector; converting at least one image of the anatomical feature after the medical cosmetic treatment to a second input image vector, calculating a difference vector by subtracting the first input image vector from the second input image vector, and normalizing the difference vector into a unit vector. If multiple difference vectors are computed from multiple before-after input image pairs, the direction vector is computed by statistical aggregation.

In some embodiments, the converting the input image into an input image vector comprises, in the computer, processing the image through a pretrained encoder.

In some embodiments, the generating the output image comprises entering the vector added, product vector and the input image vector into a generative adversarial network.

Other aspects and possible advantages will be apparent from the description and claims that follow.

DETAILED DESCRIPTION

A method according to the present disclosure begins with an actual image of a human external anatomical feature, such as the face, of a person contemplating a medical cosmetic treatment on the feature. As that term is used herein, "medical cosmetic treatment" may include any surgical procedure to alter a structural appearance of the anatomical feature, injection of a filler or other agent to alter structural appearance or to change appearance of the skin, and any other medical treatment intended to change color and/or texture appearance of the human anatomical feature.

The image may be generated using any optical imaging device known in the art for producing a printed image for subsequent digitization or an initially digitized representation of color and intensity distribution within an image field or frame. The image in digitized form may be entered into a computer or computer system for processing according to the present disclosure. The foregoing will be referred to for convenience as the "input image."

Another input to a method according to the present disclosure is the specific medical cosmetic treatment(s) to be performed on any one or more parts of the human anatomical feature (e.g., the face). As used herein, the term "aesthetic" is intended to mean any type of treatment, however administered, that changes the visual appearance of a human anatomical feature, and includes, without limitation, literal aesthetics as well as medical cosmetic treatments. As explained above, all forms of medical treatments intended to change visual appearance of a human anatomical feature are within the scope of the present disclosure.

An output of a method according to the present disclosure is an image of the same human anatomical feature (e.g., the face) as it would be expected to appear visually, after the cosmetic treatment is performed. In some embodiments, the cosmetic treatment may be an aesthetic surgical treatment. In some embodiments, the cosmetic treatment may be an aesthetic filler injection.

Figure 1:
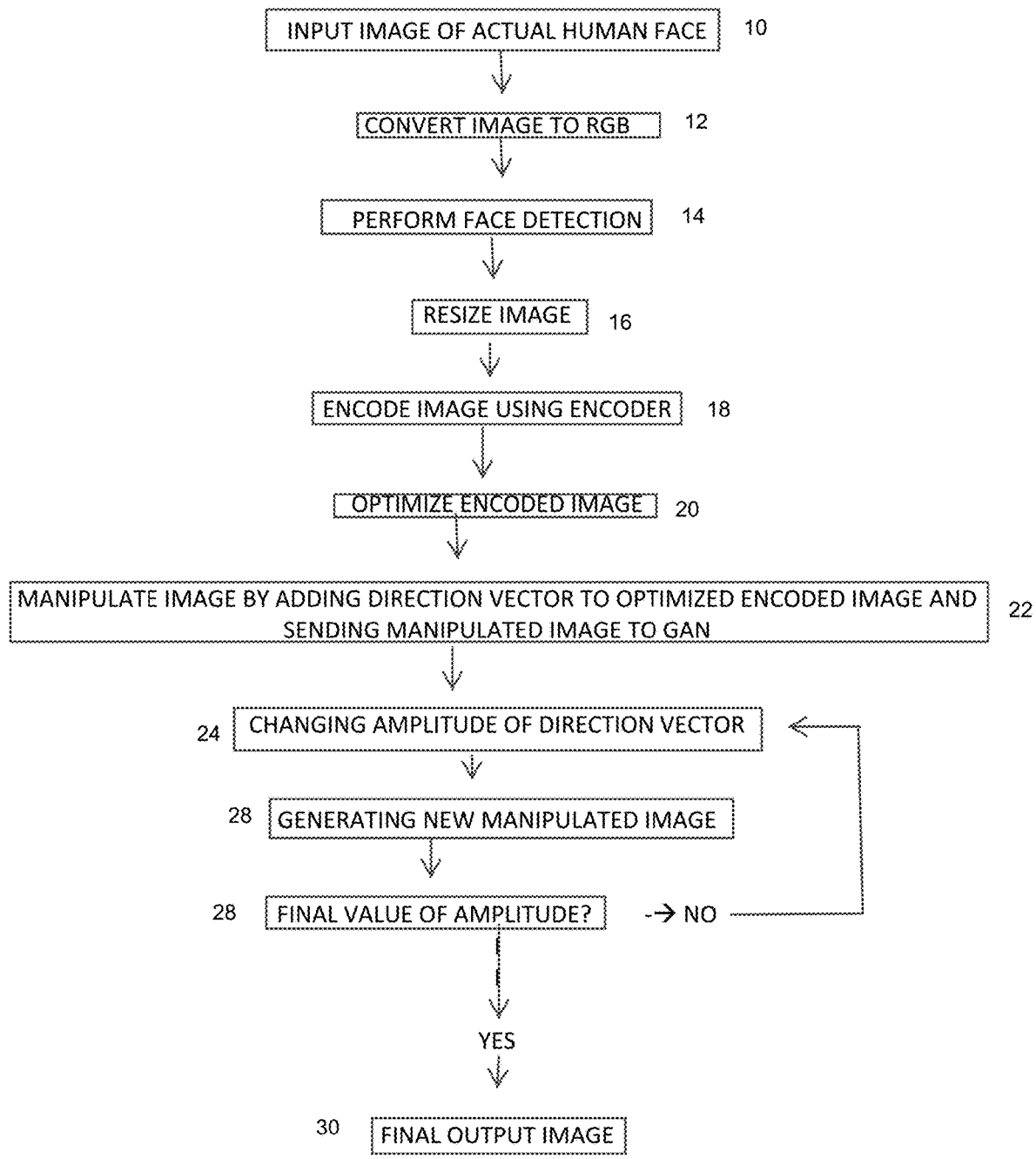
FIG. 1 shows a flow chart of an example process according to the present disclosure.

An example embodiment of a process according to the present disclosure may be better understood with reference to a flow chart FIG. 1.

In some embodiments, the input image, at 10, may be pre-processed. Pre-processing may include the following:
1. The input image may be converted, at 12, to red, green, blue (RGB) intensity distribution.
2. The human face present in the image frame may be detected, at 14, for example, using a generic face detector algorithm. Such algorithms are available, for example, as open-source code. A predetermined number, in the present example embodiment 68, facial "landmarks" may then be extracted from within the image boundary of the detected face. Landmarks may be understood as properties of predetermined anatomical portions of the human face. Landmarks are explained in U.S. Patent Application Publication No. 2021/0012097 filed by Velthuis et al. Using the landmarks, the image may be aligned to have the face moved geometrically to the center of the image frame.
3. The image may be resized, at 16, to a selected resolution, for example, 1024×1024. If required, the image may be padded or cropped to conform to the selected resolution.

In some embodiments, pre-processing may be followed, at 18, by encoding the pre-processed image. Encoding may be performed using a pretrained image to vector encoder which is trained to project an image, that is, to perform the encoding (or conversion) to a vector, into the latent space of a machine learning algorithm known as a generative adversarial network (GAN). Because the process disclosed herein has as an intended output a manipulated version (i.e., an expected visual appearance image post treatment) of the input (actual) image of a human face, an objective of the encoding is to project the actual image (i.e., the pre-processed input image) into an N×D vector space, which is the GAN latent space. Example embodiments of the encoding process may include the following.
1. Training an encoder (a neural network) which takes a sample image as input, and generates as output an N×D vector representation. This encoder is trained ahead of the actual process, trained only once and then used for each encoding flow. The pre-processed input image is then encoded using the trained encoder to generate a vector representation in the GAN latent space. The parameters represented by N and D and the values of N and D are a matter of discretion for the method designer and are not intended to limit the scope of the present disclosure. Representative parameters may be related to the resolution of the input image and the resolution of the intended output image. For purposes of this description, the N×D vector generated from the input image may be referred to as an "input image vector."
2. Optimizing the encoded image, at 20, may include fine-tuning the previously encoded vector representation (the input image vector) to reflect the original image better. Optimization may be performed iteratively and may be based on a loss function. In some embodiments, such loss function may be the mean squared loss between the actual pixel values or extracted higher-level features of the preprocessed input image and the image generated from the current vector representation (current input image vector) using the GAN to transform the vector representation back to the image space. The GAN will be explained further below. The present example embodiment may use stochastic gradient descent to indicate changes to the current vector representation at each iteration of the optimizing to minimize the loss function in a relatively small number of iterations.

3. Optimization as in (2) may be performed for either (a) a predetermined number of iterations or (b) until the loss function reduces to below a predetermined threshold.

Image Manipulation and Expected Image Generation: After the optimized N×D (input image) vector representation of the input image is generated, manipulation of the optimized input image vector, at 22, can be performed by simple vector addition of a direction vector to the optimized input image (N×D) vector representation, which may be referred to as a "manipulated image vector." The output of the vector addition, that is, the manipulated image vector, may be used to generate an output image that emulates effects of the medical cosmetic treatment. The output image may be generated by inputting the manipulated image vector, as explained above, to a machine learning algorithm known as a generative adversarial network (GAN). The GAN generates as its output the manipulated image, which may be stored and/or displayed in any known manner for image storage and display. The GAN may also be used in the process of optimizing the generation of a vector representation of the input image, as explained above.

It should be noted that the direction vector only defines a direction in latent space, and acts as a unit vector. An additional input may be an amplitude for the direction vector which directly changes the magnitude of the image manipulation. At 24, the amplitude may be changed, and at 26, a new manipulated image may be generated using the GAN. At 28, if the amplitude is the final value of the amplitude, determined as explained below, then the process halts at 30 and the then existing GAN output image is used as the final output image.

Example procedures for determining the amplitude of the direction vector to generate the manipulated image vector may include the following.

1. Iteratively increase the amplitude of the direction vector, vector add it to the optimized N×D vector representation of the input image (the input image vector), and send the manipulated image vector representation to the GAN to generate a manipulated image, and repeat the foregoing with incrementally increased amplitude until a final value of the amplitude is reached.

Figure 2:
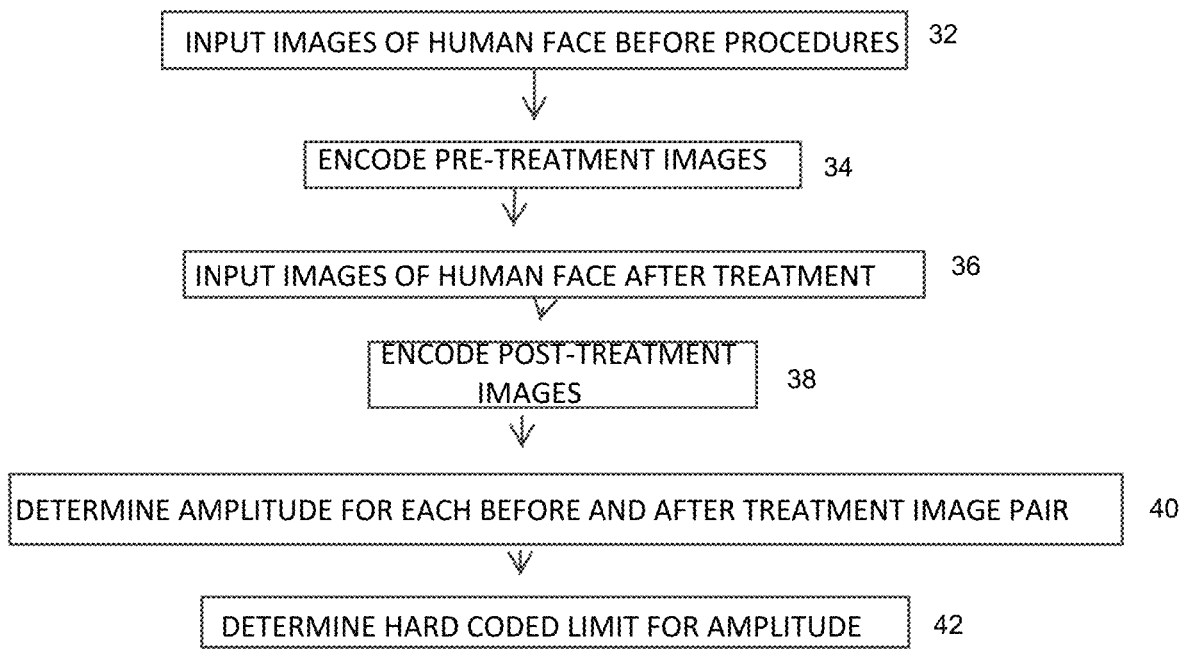
FIG. 2 shows a flow chart of an example process for determining hard coded limits to an amplitude for scaling a direction vector in the process of FIG. 1.
Figure 3:
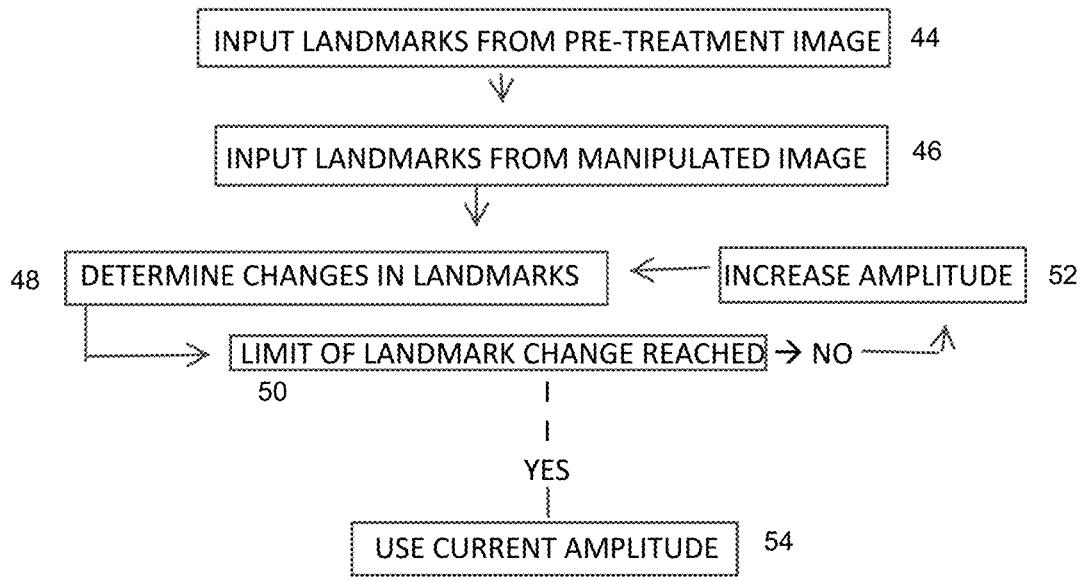
FIG. 3 shows a flow chart of an example process for determining the amplitude for the process in FIG. 1.

2. The final value of the amplitude may be obtained in various embodiments using such examples as:

a. Referring to FIG. 2, a hard-coded upper limit for the amplitude may be obtained as follows: While selecting the direction vector for a specific medical cosmetic treatment, the process may use as input actual images of a human person taken before, at 32, and after, at 34, a same medical cosmetic treatment, to form one or more image pairs. At 36, and 38, respectively, each of the before treatment and after treatment images is encoded using, for example, the previously described trained encoder. Difference vectors between the image vectors in each image pair are obtained by subtracting the before treatment vector representation from the after treatment vector representation in each image pair. For each before treatment and after treatment image pair, an amplitude value is calculated using the difference vector and the previously identified direction vector. A final value of the hard-coded upper limit is then selected using a distribution of the amplitude values calculated as just explained. (An upper limit for the amplitude may be determined using the distribution of the amplitude values calculated by computing the mean and standard deviation of the values and calculating the mean plus three standard deviations.

b. Referring to FIG. 3, change in landmarks may be used: Changes in the landmarks on the face that are associated with the region of the face that the aesthetic treatment is affecting are evaluated both before, at 44, and after, at 46 a treatment is performed using the input image and the manipulated image. When a difference or ratio, determined at 48, between selected landmarks reaches a predefined limit at 50, further changes in landmarks are terminated at 54, and the current amplitude value is used. If at 50 the limit has not been reached, the landmarks may be changed at 52, and the process returns at 48, to the act of determining changes in the landmarks. The foregoing ratio or difference may be understood as being related to distances between various specific points on the anatomical feature, e.g., the human face. It is understood by medical practitioners that certain distances or ratios of distances between certain anatomical features are within empirically determined limits. Such empirically determined limits may be used as the limit at 50 in FIG. 3.

c. Change in color and texture: When the change in the color and the texture of the affected region reaches a predefined limit, the procedure is stopped and the then-current amplitude value is used as the final value of amplitude. Predefined limits for landmarks and color may be obtained for example using before treatment and after treatment images of human anatomical features from the face image data set.

3. After determining the final value of the amplitude, a final manipulated image (the output image) is generated by sending the resultant manipulated image vector as input to the GAN. The resultant manipulated image vector is obtained, as explained above, by vector addition of the product of the direction and amplitude and the original N×D representation of the input image (i.e., the input image vector). The resultant manipulated image vector is then processed by the GAN to generate the manipulated image.

Figure 4:
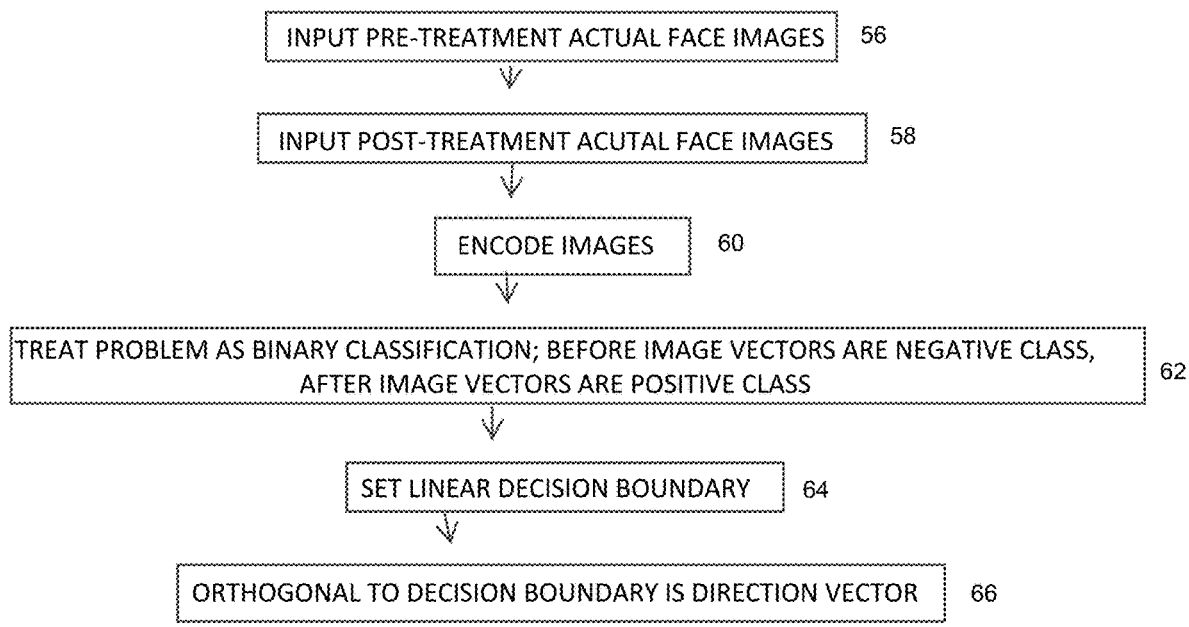
FIG. 4 shows a flow chart of a process for determining direction vectors that correspond to specific cosmetic treatments.

Identification of a direction vector for each type of aesthetic (or cosmetic medical) treatment may be determined as explained with reference to FIGS. 4A and 4B: The direction may be determined using vector representations of actual before treatment images and actual after treatment images of persons who had undergone such various treatment. Direction vectors for such various medical cosmetic treatments so determined may be stored in a database (e.g., as explained with reference to FIG. 5) for later access in initializing the disclosed process for any new input image. Example embodiments of a process for determining the direction vector may be as according to one of the following methods:

Method 1 (FIG. 4A):

1. Each before treatment image, input at 56, and each after treatment image, at 58, is encoded (converted, or projected) into the N×D vector space, at 60, using the encoding process explained above.

2. The direction vector determination is treated as a binary classification at 62 where all N×D latent vectors for the before and after images represent the negative and the positive class, respectively.

3. A linear decision boundary is determined at 64 and the vector that is orthogonal to the decision boundary is determined at 66 to be the direction for the specific medical cosmetic treatment.

Method 2 (FIG. 4-B):

1. Each before treatment image, at 56A, and each after treatment image, at 58A is converted into a vector, e.g., a N×D vector, at 60A, using the encoder as explained above.

2. A difference vector for each before treatment and after treatment vector pair is calculated, at 62A, by subtracting the before treatment vector from the after treatment vector.

3. Each difference vector is normalized, at 64A to a unit vector.

4. The final direction vector is then computed, at 66A, as the statistical aggregation of unit difference vectors, such as taking the mean or median of the unit difference vectors.

It should be noted that while description of image encoding and processing according to the present disclosure is made in terms of entire images, it is within the scope of the present disclosure to process only a selected portion of an image to generate a visual representation of expected appearance of such selected part of an image. Accordingly, "image" as used in the present disclosure may mean all pixels within the frame of an object for which an image is made or any selected subset thereof. Further, while the present disclosure sets forth a process for generating a visual representation of expected appearance corresponding to a single medical cosmetic treatment on a chosen anatomical feature, it is within the scope of the present disclosure to process a single input image as a plurality of subset images, each having a different anatomical feature, and to generate expected visual appearance images for each subset image using a different selected medical cosmetic procedure. Such subset image processing may be performed sequentially or simultaneously, while remaining consistent with the scope of the present disclosure.

Figure 5:
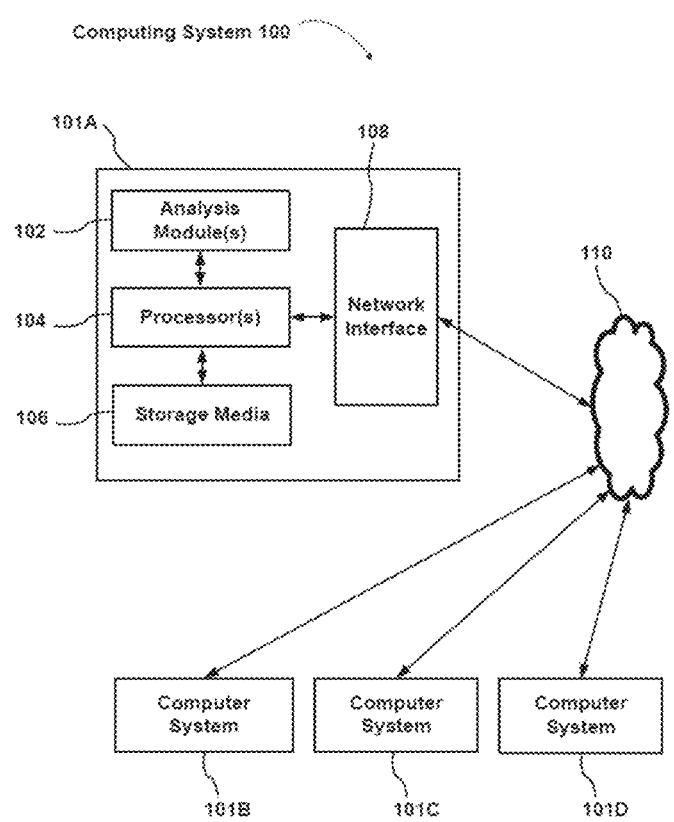
FIG. 5 shows an example embodiment of a computer system that may be used to perform a method according to the present disclosure.

FIG. 5 shows an example embodiment of a computing system 100 that may be used to perform the actions explained with reference to FIGS. 1 through 4. The computing system 100 may be an individual computer system 101A or an arrangement of distributed computer systems. The individual computer system 101A may include one or more analysis modules 102 that may be configured to perform various tasks according to some embodiments, such as the tasks explained with reference to FIG. 5. To perform these various tasks, the analysis module 102 may operate independently or in coordination with one or more processors 104, which may be connected to one or more storage media 106. A display device such as a graphic user interface of any known type may be in signal communication with the processor 104 to enable user entry of commands and/or data and to display results of execution of a set of instructions according to the present disclosure.

The processor(s) 104 may also be connected to a network interface 108 to allow the individual computer system 101A to communicate over a data network 110 with one or more additional individual computer systems and/or computing systems, such as 101B, 101C, and/or 101D (note that computer systems 101B, 101C and/or 101D may or may not share the same architecture as computer system 101A, and may be located in different physical locations, for example, computer systems 101A and 101B may be at a well drilling location, while in communication with one or more computer systems such as 101C and/or 101D that may be located in one or more data centers, and/or located in varying countries on different continents).

A processor may include, without limitation, a microprocessor, microcontroller, processor module or subsystem, programmable integrated circuit, programmable gate array, or another control or computing device.

The storage media 106 may be implemented as one or more computer-readable or machine-readable storage media, e.g., non-transitory storage media. The storage media may comprise logic operable to cause the computer system to perform the actions described above with reference to FIGS. 1 through 4. Note that while in the example embodiment of FIG. 5 the storage media 106 are shown as being disposed within the individual computer system 101A, in some embodiments, the storage media 106 may be distributed within and/or across multiple internal and/or external enclosures of the individual computing system 101A and/or additional computing systems, e.g., 101B, 101C, 101D. Storage media 106 may include, without limitation, one or more different forms of memory including semiconductor memory devices such as dynamic or static random access memories (DRAMs or SRAMs), erasable and programmable read-only memories (EPROMs), electrically erasable and programmable read-only memories (EEPROMs) and flash memories; magnetic disks such as fixed, floppy and removable disks; other magnetic media including tape; optical media such as compact disks (CDs) or digital video disks (DVDs); or other types of storage devices. Note that computer instructions to cause any individual computer system or a computing system to perform the tasks described above may be provided on one computer-readable or machine-readable storage medium, or may be provided on multiple computer-readable or machine-readable storage media distributed in a multiple component computing system having one or more nodes. Such computer-readable or machine-readable storage medium or media may be considered to be part of an article (or article of manufacture). An article or article of manufacture can refer to any manufactured single component or multiple components. The storage medium or media can be located either in the machine running the machine-readable instructions, or located at a remote site from which machine-readable instructions can be downloaded over a network for execution.

It should be appreciated that computing system 100 is only one example of a computing system, and that any other embodiment of a computing system may have more or fewer components than shown, may combine additional components not shown in the example embodiment of FIG. 5, and/or the computing system 100 may have a different configuration or arrangement of the components shown in FIG. 5. The various components shown in FIG. 5 may be implemented in hardware, software, or a combination of both hardware and software, including one or more signal processing and/or application specific integrated circuits.

Further, the acts of the processing methods described above may be implemented by running one or more functional modules in information processing apparatus such as general purpose processors or application specific chips, such as ASICs, FPGAs, PLDs, or other appropriate devices. These modules, combinations of these modules, and/or their combination with general hardware are all included within the scope of the present disclosure.

In light of the principles and example embodiments described and illustrated herein, it will be recognized that the example embodiments can be modified in arrangement and detail without departing from such principles. The foregoing discussion has focused on specific embodiments, but other configurations are also contemplated. In particular, even though expressions such as in "an embodiment," or the like are used herein, these phrases are meant to generally reference embodiment possibilities, and are not intended to limit the disclosure to particular embodiment configurations. As used herein, these terms may reference the same or different embodiments that are combinable into other embodiments. As a rule, any embodiment referenced herein is freely combinable with any one or more of the other embodiments referenced herein, and any number of features of different embodiments are combinable with one another, unless indicated otherwise. Although only a few examples have been described in detail above, those skilled in the art will readily appreciate that many modifications are possible within the scope of the described examples. Accordingly, all such modifications are intended to be included within the scope of this disclosure as defined in the following claims.

What is claimed is:

1. A method for generating an image of a human anatomical feature representative of expected visual appearance of the human anatomical feature after performance of a medical cosmetic treatment, the method comprising:
   sending as input to a computer an image of the human anatomical feature prior to performing the medical cosmetic treatment;
   in the computer, converting the input image prior to the medical cosmetic treatment into an input image vector;
   in the computer, selecting a direction vector corresponding to the medical cosmetic treatment, wherein the direction vector is determined by converting each of a plurality of corresponding images of the anatomical feature before the medical cosmetic treatment to a first input image vector, converting each of a plurality of corresponding images of the anatomical feature after the medical cosmetic treatment to a second input image vector, calculating a difference vector by subtracting the second input image vector from the first input image vector, normalizing the difference vector into a unit vector, and for the plurality of corresponding images before and after the medical cosmetic treatment, performing statistical aggregation on the difference vectors;
   in the computer, determining an amplitude of the direction vector;
   in the computer, multiplying the direction vector by the determined amplitude to obtain a product vector;
   in the computer, vector adding the product vector to the input image vector; and
   in the computer, generating an output image corresponding to the expected visual appearance from the vector added, product vector and the input image vector.

2. The method of claim 1 further comprising optimizing the converting by, in the computer:
   (a) generating an optimizing image from the input image vector;
   (b) comparing the optimizing image with the input image to calculate a loss function;
   (c) changing the input image vector and repeating the generating the optimizing image; and
   (d) repeating (a), (b) and (c) until either (i) a value of the loss function falls below a predetermined threshold or (ii) (a), (b) and (c) are repeated a selected number of times.

3. The method of claim 1 wherein the determining the amplitude comprises, in the computer:
   (a) converting a pre treatment image of a corresponding human anatomical feature to an input vector;
   (b) initially estimating an amplitude and generating an intermediate product vector by combining the initially estimated amplitude with the direction vector;
   (c) adding the intermediate product vector to the converted input vector;
   (d) generating an output image from the intermediate product vector;
   (e) determining a change in landmark positions, color and texture between the pre treatment image and the output image; and
   (f) adjusting the amplitude and repeating (b), (c), (d), and (e) until the change in at least one of the landmarks, color and texture reaches a predefined threshold or the amplitude reaches predetermined upper limit.

4. The method of claim 1 wherein the determining the amplitude comprises, in the computer:
   (a) converting pre treatment images and corresponding post treatment images of corresponding human anatomical features to vectors;
   (b) calculating a difference vector between each converted pre treatment image and each corresponding converted post treatment converted image;
   (c) calculating an amplitude for each difference vector; and
   (d) selecting an upper limit of the amplitude using a distribution of the amplitudes values calculated in (c).

5. The method of claim 1 wherein the generating the output image comprises entering the vector added, product vector and input image vector into a generative adversarial network.

6. A computer program stored in a non-transitory computer readable medium for generating an image of a human anatomical feature representative of expected visual appearance of the human anatomical feature after performance of a medical cosmetic treatment, the program having logic operable to cause a programmable computer to perform actions comprising:
   receiving as input to the computer an image of the human anatomical feature prior to performing the medical cosmetic treatment;
   in the computer, converting the input image into an input image vector;
   in the computer, selecting a direction vector corresponding to the medical cosmetic treatment, wherein the direction vector is determined by converting each of a plurality of corresponding images of the anatomical feature before the medical cosmetic treatment to a first input image vector, converting each of a plurality of corresponding images of the anatomical feature after the medical cosmetic treatment to a second input image vector, calculating a difference vector by subtracting the second input image vector from the first input image vector, normalizing the difference vector into a unit vector, and for the plurality of corresponding images before and after the medical cosmetic treatment, performing statistical aggregation on the difference vectors;
   in the computer, determining an amplitude of the direction vector;
   in the computer, multiplying the direction vector by the determined amplitude to obtain a product vector;
   in the computer, vector adding the product vector to the input image vector; and
   in the computer, generating an output image corresponding to the expected visual appearance from the vector added, product vector and the input image vector.

7. The computer program of claim 6 further comprising logic operable to cause the computer to optimize the converting by:
   (a) generating an optimizing image from the input image vector;
   (b) comparing the optimizing image with the input image to calculate a loss function;

(c) changing the input image vector and repeating the generating the optimizing image; and (d) repeating (a), (b) and (c) until either (i) a value of the loss function falls below a predetermined threshold or (ii) (a), (b) and (c) are repeated a selected number of times.

8. The computer program of claim 6 wherein the determining the amplitude comprises:

(a) converting a pre treatment image of a corresponding human anatomical feature to an input vector;

(b) initially estimating an amplitude and generating an intermediate product vector by combining the initially estimated amplitude with the input vector;

(c) vector adding the intermediate product vector to the converted input vector;

(d) generating an output image from the intermediate product vector;

(e) determining a change in landmark positions, color and texture between the pre treatment image and the output image; and (f) adjusting the amplitude and repeating (b), (c), (d) and (e) until the change in at least one of the landmarks, color and texture reaches a predefined threshold or the amplitude reaches predetermined upper limit.

9. The computer program of claim 6 wherein the determining the amplitude comprises, for the medical cosmetic treatment:

(a) converting pre treatment images and corresponding post treatment images of corresponding human anatomical features to vectors;

(b) calculating a difference vector between each converted pre treatment image and each corresponding post treatment converted image;

(c) calculating an amplitude for each difference vector; and (d) selecting an upper limit of the amplitude using a distribution of the amplitudes values calculated in (c).

10. The computer program of claim 6 wherein the generating the output image comprises entering the vector added, product vector and input image vector into a generative adversarial network.

11. A method for generating an image of a human anatomical feature representative of expected visual appearance of the human anatomical feature after performance of a medical cosmetic treatment, the method comprising:

sending as input to a computer an image of the human anatomical feature prior to performing the medical cosmetic treatment;

in the computer, converting the input image prior to the medical cosmetic treatment into an input image vector;

in the computer, selecting a direction vector corresponding to the medical cosmetic treatment;

in the computer, determining an amplitude of the direction vector;

in the computer, multiplying the direction vector by the determined amplitude to obtain a product vector;

in the computer, vector adding the product vector to the input image vector; and in the computer, generating an output image corresponding to the expected visual appearance from the vector added, product vector and the input image vector;

wherein the direction vector is determined, for the medical cosmetic treatment:

converting at least one image of the anatomical feature before the medical cosmetic treatment to a first input image vector;

converting at least one image of the anatomical feature after the medical cosmetic treatment to a second input image vector;

treating the first image vector and the second image vector as a binary classification wherein the before and after images represent a negative and a positive class, respectively; and setting a linear decision and determining a vector that is orthogonal to the linear decision boundary.

12. The method of claim 11 wherein the determining the amplitude comprises, in the computer:

(a) converting a pre treatment image of a corresponding human anatomical feature to an input vector;

(b) initially estimating an amplitude and generating an intermediate product vector by combining the initially estimated amplitude with the direction vector;

(c) adding the intermediate product vector to the converted input vector;

(d) generating an output image from the intermediate product vector;

(e) determining a change in landmark positions, color and texture between the pre treatment image and the output image; and (f) adjusting the amplitude and repeating (b), (c), (d), and (e) until the change in at least one of the landmarks, color and texture reaches a predefined threshold or the amplitude reaches predetermined upper limit.

13. The method of claim 11 wherein the determining the amplitude comprises, in the computer:

(a) converting pre treatment images and corresponding post treatment images of corresponding human anatomical features to vectors;

(b) calculating a difference vector between each converted pre treatment image and each corresponding converted post treatment converted;

(c) calculating an amplitude for each difference vector; and (d) selecting an upper limit of the amplitude using a distribution of the amplitudes values calculated in (c).

14. A computer program stored in a non-transitory computer readable medium for generating an image of a human anatomical feature representative of expected visual appearance of the human anatomical feature after performance of a medical cosmetic treatment, the program having logic operable to cause a programmable computer to perform actions comprising:

receiving as input to the computer an image of the human anatomical feature prior to performing the medical cosmetic treatment;

in the computer, converting the input image into an input image vector;

in the computer, selecting a direction vector corresponding to the medical cosmetic treatment;

in the computer, determining an amplitude of the direction vector;

in the computer, multiplying the direction vector by the determined amplitude to obtain a product vector;

in the computer, vector adding the product vector to the input image vector; and in the computer, generating an output image corresponding to the expected visual appearance from the vector added, product vector and the input image vector;

wherein the direction vector is determined, for the medical cosmetic treatment:

converting at least one image of the anatomical feature before the medical cosmetic treatment to a first input image vector;

converting at least one image of the anatomical feature after the medical cosmetic treatment to a second input image vector;

treating the first image vector and the second image vector as a binary classification wherein the before and after images represent a negative and a positive class, respectively; and setting a linear decision and determining a vector that is orthogonal to the linear decision boundary.

15. The computer program of claim 14 wherein the determining the amplitude comprises:

(a) converting a pre treatment image of a corresponding human anatomical feature to an input vector;

(b) initially estimating an amplitude and generating an intermediate product vector by combining the initially estimated amplitude with the input vector;

(c) vector adding the intermediate product vector to the converted input vector;

(d) generating an output image from the intermediate product vector;

(e) determining a change in landmark positions, color and texture between the pre treatment image and the output image; and (f) adjusting the amplitude and repeating (b), (c), (d) and (e) until the change in at least one of the landmarks, color and texture reaches a predefined threshold or the amplitude reaches predetermined upper limit.

16. The computer program of claim 14 wherein the determining the amplitude comprises, for the medical cosmetic treatment:

(a) converting pre treatment images and corresponding post treatment images of corresponding human anatomical features to vectors;

(b) calculating a difference vector between each converted pre treatment image and each corresponding post treatment converted image;

(c) calculating an amplitude for each difference vector; and (d) selecting an upper limit of the amplitude using a distribution of the amplitudes values calculated in (c).

* * * * *